(12) United States Patent
Steinberg et al.

(10) Patent No.: US 11,806,113 B1
(45) Date of Patent: Nov. 7, 2023

(54) THERMOACOUSTIC PROBE

(71) Applicant: ENDRA Life Sciences Inc., Ann Arbor, MI (US)

(72) Inventors: Idan Steinberg, Superior Charter Township, MI (US); Michael M. Thornton, London (CA)

(*) Notice: Subject to any disclaimer, the term of this patent is extended or adjusted under 35 U.S.C. 154(b) by 0 days.

(21) Appl. No.: 18/222,363

(22) Filed: Jul. 14, 2023

Related U.S. Application Data

(63) Continuation-in-part of application No. 17/865,034, filed on Jul. 14, 2022, now Pat. No. 11,730,374.

(60) Provisional application No. 63/468,855, filed on May 25, 2023.

(51) Int. Cl.
*A61B 5/00* (2006.01)

(52) U.S. Cl.
CPC .......... *A61B 5/0093* (2013.01); *A61B 5/4244* (2013.01)

(58) Field of Classification Search
CPC ....... A61B 5/0093; A61B 5/0095; A61B 5/05; A61B 5/0507; A61B 5/4244; A61B 5/489; A61B 18/04; A61B 8/00; A61B 8/5261
See application file for complete search history.

(56) References Cited

U.S. PATENT DOCUMENTS

2021/0077018 A1* 3/2021 Cho .................. A61B 5/05
2021/0244384 A1* 8/2021 Barnes .............. G01K 11/22

OTHER PUBLICATIONS

Georg Wissmeyer, Miguel A. Pleitez, Amir Rosenthal, and Vasilis Ntziachristos; "Looking at sound: optoacoustics with all-optical ultrasound detection"; Light: Science & Applications (2018) 7:53; DOI 10.1038/s41377-018-0036-7; pp. 1-16.

* cited by examiner

*Primary Examiner* — Peter Luong
(74) *Attorney, Agent, or Firm* — Stanley E. Jelic

(57) ABSTRACT

A thermoacoustic probe for a thermoacoustic imaging system, the probe including: a radio-frequency (RF) applicator having an insert, wherein the applicator is configured to transmit at least one radio frequency source; an electromagnetic matching layer coupled to the insert of the RF applicator; an optical transducer that is coupled to the electromagnetic matching layer; and an acoustic matching layer that is coupled to the optical transducer.

29 Claims, 7 Drawing Sheets

THERMOACOUSTIC PROBE

CROSS REFERENCE TO RELATED APPLICATION

This application is a continuation-in-part of pending U.S. non-provisional application Ser. No. 17/865,034, filed Jul. 14, 2022, and also claims the priority benefit of provisional patent application 63/468,855 filed May 25, 2023, both of which are herein incorporated by reference in their entirety.

TECHNICAL FIELD

This disclosure relates generally to thermoacoustic imaging, and more particularly to system and method for thermoacoustic imaging using a thermoacoustic probe to deposit energy and receive signals.

BACKGROUND

The statements in this section merely provide background information related to the present disclosure and may not constitute prior art.

In high frequency systems, it is common to employ waveguides to guide electromagnetic waves or sound with minimal loss of energy by restricting expansion of the electromagnetic waves propagating within the waveguides to one or two dimensions. Depending on the nature of the electromagnetic waves to be propagated, the waveguides may take different forms. In many instances, filters are employed to allow electromagnetic waves at some frequencies to pass and travel along the waveguides, while rejecting electromagnetic waves at other frequencies. For example, when propagating radio frequency (RF) waves, hollow, open-ended, conductive metal waveguides are often employed. In some instances, to provide the desired filtering, these hollow metal waveguides are fitted with a solid insert formed of high dielectric constant material.

Waveguides such as those described above have been employed in thermoacoustic imaging systems. Thermoacoustic imaging is an imaging modality that provides information relating to the thermoelastic properties of tissue. Thermoacoustic imaging uses short pulses of electromagnetic energy, such as RF pulses, directed into a subject to heat absorbing features within the subject rapidly, which in turn induces acoustic pressure waves that are detected using acoustic receivers such as one or more thermoacoustic or ultrasound transducer arrays. The detected acoustic pressure waves are analyzed through signal processing, and processed for presentation as thermoacoustic images that can be interpreted by an operator.

In order to direct RF pulses into the subject during thermoacoustic imaging, a radio frequency (RF) applicator employing a waveguide is coupled to tissue adjacent a region of interest (116) within the subject to be imaged. Sub-optimal coupling of the RF applicator to the tissue may cause issues such as inefficient energy transfer, reduced heating rates, reduced signal intensity, non-uniform energy deposition, tissue hotspots, tissue overheating, RF power supply damage, and poor image quality. Factors that lead to sub-optimal coupling of the RF applicator to the tissue include variability in the size of the subject, the size of tissue within the subject, the geometry of tissue within the subject, the composition of tissue within the subject, etc.

The strong electromagnetic field inside the applicator and in its closest vicinity (the top layers of the medium to be imaged) as well as the high conductivity of the skin layer generates a strong spurious acoustic wave close to the applicator's front face. This wave, which is of no clinical interest, propagates through the tissue and overshadows the desired thermoacoustic signals from various constituents, thus interfering with the measurement.

Many academic systems utilize a split-configuration where the applicator is either facing the acoustic sensor (opposed geometry) or at 90 degrees to the applicator (perpendicular geometry). Opposed geometry ensures that the interfering signal will arrive last and thus it is temporarily separated from the signals of interest. Perpendicular geometry configuration ensures that only a side-scattered wave will reach the detector and thus reduces the received interference greatly.

The shortcoming of both configurations however, is that it is more difficult to perform in a clinical setting with a handheld. Hence a need exists for an improved thermoacoustic probe for a thermoacoustic imaging system.

SUMMARY

A thermoacoustic probe for a thermoacoustic imaging system comprising: a radio-frequency (RF) applicator having an insert, wherein the applicator is configured to transmit at least one radio frequency source; an electromagnetic matching layer coupled to the insert of the RF applicator; an optical transducer that is coupled to the electromagnetic matching layer; and an acoustic matching layer that is coupled to the optical transducer.

In one embodiment, the acoustic matching layer is configured to limit acoustic attenuation to 0.01 to 0.5 dB/(cm*MHz) with an acoustic frequency between 50 kHz and 25 MHz.

In one embodiment, the optical transducer is coupled to an RF emitter at an aperture of the RF applicator.

In one embodiment, a cross-sectional shape of the acoustically matching layer comprises a triangular shape with a center vertex between 90 degrees and 180 degrees.

In one embodiment, portions of the acoustically matching layer are formed in convex shape.

In one embodiment, the acoustically matching layer has at least one tapered edge.

In one embodiment, the acoustic matching layer, at a frequency range between 15 MHz and 2.5 GHz, has a real part of permittivity from 5 to 65 and an imaginary part of permittivity from 0.01 to 60.

In one embodiment, the acoustic matching layer, at a frequency range between 50 kHz and 25 MHz, has an acoustic impedance between 1.2 MRayl and 1.8 MRayl.

In one embodiment, the acoustic matching layer is formed of an open-cell foam.

In one embodiment, the acoustic matching layer is formed of an acoustic anechoic absorber.

In one embodiment, the acoustic matching layer is formed of a rubber-based vibration isolation material.

In one embodiment, the electromagnetic matching layer, at a frequency range between 15 MHz and 2.5 GHz, has a real part of permittivity from 5 to 65 and an imaginary part of permittivity from 0.01 to 60.

In one embodiment, the electromagnetic matching layer is formed of an elastomer material with a permittivity from 23 to 60.

In one embodiment, the electromagnetic matching layer is formed of a ceramic material.

In one embodiment, the electromagnetic matching layer is formed of a composite material which contains particles with a permittivity from 23 to 60 embedded in a solid matrix.

In one embodiment, the optical transducer is configured to receive light-based information corresponding to at least one of light intensity, polarization, phase, frequency, direction, and spatial distribution.

In one embodiment, a thermoacoustic probe for a thermoacoustic imaging comprises: a radio-frequency (RF) applicator having an insert, wherein the applicator is configured to transmit at least one radio frequency source; an electromagnetic matching layer having first and second opposing sides, wherein the first opposing side of the electromagnetic matching layer is coupled to the insert of the RF applicator; an optical transducer having first and second opposing sides, wherein a first opposing side of the optical transducer is coupled to the second opposing side of the electromagnetic matching layer; and an acoustic matching layer that is coupled to the second opposing side of the optical transducer.

In one embodiment, the optical transducer is configured to receive light-based information corresponding to at least one of light intensity, polarization, phase, frequency, direction, and spatial distribution.

In one embodiment, the first opposing side of the electromagnetic matching layer is coupled to the insert of the RF applicator using an adhesive, the first opposing side of the optical transducer is coupled to the second opposing side of the electromagnetic matching layer using an adhesive, and the acoustic matching layer is coupled to the second opposing side of the optical transducer using an adhesive.

In one embodiment, the acoustic matching layer is configured to limit acoustic attenuation to 0.01 to 0.5 dB/(cm*MHz) with an acoustic frequency between 50 kHz and 25 MHz.

In one embodiment, the optical transducer is coupled to an RF emitter at an aperture of the RF applicator.

In one embodiment, at least a portion of a cross-sectional shape of the acoustically matching layer comprises a triangular shape with a center vertex between 90 degrees and 180 degrees.

In one embodiment, portions of the acoustically matching layer are formed in convex shape.

In one embodiment, the acoustically matching layer has at least one tapered edge.

In one embodiment, the acoustic matching layer, at a frequency range between 15 MHz and 2.5 GHz, has a real part of permittivity from 5 to 65 and an imaginary part of permittivity from 0.01 to 60.

In one embodiment, the acoustic matching layer, at a frequency range between 50 kHz and 25 MHz, has an acoustic impedance between 1.2 MRayl and 1.8 MRayl.

In one embodiment, the acoustic matching layer is formed of an open-cell foam.

In one embodiment, the acoustic matching layer is formed of an acoustic anechoic absorber.

In one embodiment, the acoustic matching layer is formed of a rubber-based vibration isolation material.

This summary is provided merely to introduce certain concepts and not to identify key or essential features of the claimed subject matter.

BRIEF DESCRIPTION OF THE DRAWINGS

One or more embodiments will now be described, by way of example, with reference to the accompanying drawings, in which.

DETAILED DESCRIPTION

Figure 1:
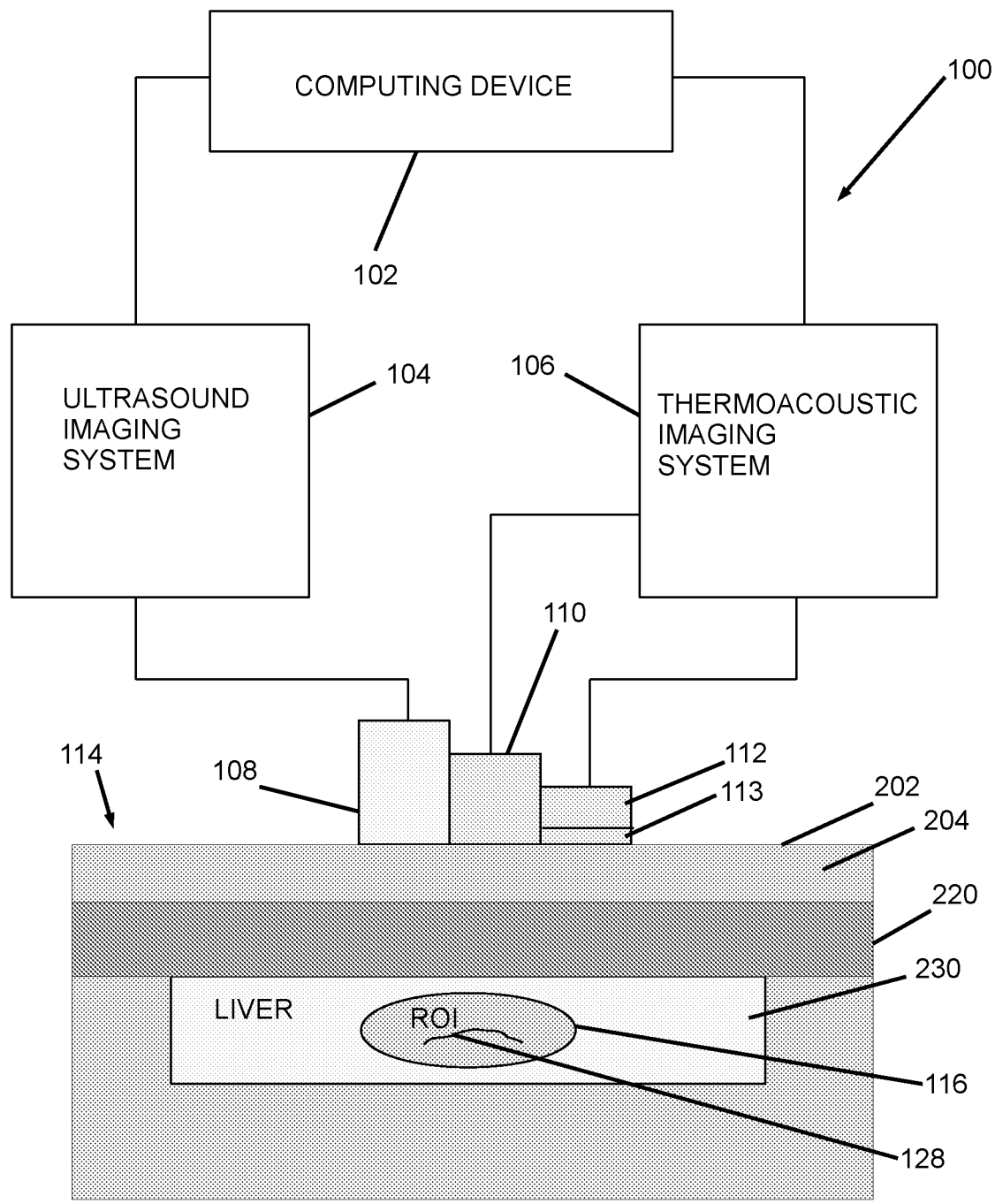
FIG. 1 schematically shows an exemplary imaging system and an exemplary region of interest in a liver with a blood vessel.

Reference throughout this specification to "one embodiment," "an embodiment," or similar language means that a particular feature, structure, or characteristic described in connection with the embodiment is included in at least one embodiment of the subject matter of the present disclosure. Appearances of the phrases "in one embodiment," "in an embodiment," and similar language throughout this specification may, but do not necessarily, all refer to the same embodiment. The term "based upon" is not exclusive and allows for being based on additional factors not described, unless the context clearly dictates otherwise. Additionally, in the subject description, the word "exemplary" is used to mean serving as an example, instance or illustration.

Moreover, unless explicitly stated to the contrary, examples or embodiments "comprising" or "having" or "including" an element or feature or a plurality of elements or features having a particular property may include additional elements or features not having that property. Also, it will be appreciated that the terms "comprises", "has", "includes" means "including but not limited to" and the terms "comprising", "having" and "including" have equivalent meanings.

As used herein, the term "and/or" can include any and all combinations of one or more of the associated listed elements or features.

It will be understood that when an element or feature is referred to as being "on", "attached" to, "connected" to, "coupled" with, "contacting", etc. another element or feature, that element or feature can be directly on, attached to, connected to, coupled with or contacting the other element or feature or intervening elements may also be present. Further, the "coupled" or "coupling" may be accomplished using an adhesive layer. In contrast, when an element or feature is referred to as being, for example, "directly on", "directly attached" to, "directly connected" to, "directly coupled" with or "directly contacting" another element of feature, there are no intervening elements or features present.

It will be understood that spatially relative terms, such as "under", "below", "lower", "over", "above", "upper", "front", "back" and the like, may be used herein for ease of description to describe the relationship of an element or feature to another element or feature as illustrated in the figures. The spatially relative terms can however, encompass different orientations in use or operation in addition to the orientations depicted in the figures.

Reference herein to "example" means that one or more feature, structure, element, component, characteristic and/or operational step described in connection with the example is included in at least one embodiment and/or implementation of the subject matter according to the subject disclosure. Thus, the phrases "an example," "another example," and similar language throughout the subject disclosure may, but do not necessarily, refer to the same example. Further, the subject matter characterizing any one example may, but does not necessarily, include the subject matter characterizing any other example.

Reference herein to "configured" denotes an actual state of configuration that fundamentally ties the element or feature to the physical characteristics of the element or feature preceding the phrase "configured to".

Unless otherwise indicated, the terms "first," "second," etc. are used herein merely as labels, and are not intended to impose ordinal, positional, or hierarchical requirements on the items to which these terms refer. Moreover, reference to a "second" item does not require or preclude the existence of a lower-numbered item (e.g., a "first" item) and/or a higher-numbered item (e.g., a "third" item).

As used herein, the terms "approximately" and "about" represent an amount close to the stated amount that still performs the desired function or achieves the desired result. For example, the terms "approximately" and "about" may refer to an amount that is within engineering tolerances that would be readily appreciated by a person of ordinary skill in the art.

Various embodiments of the present invention will be described in detail with reference to the drawings, where like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

Referring now to the drawings, wherein the depictions are for the purpose of illustrating certain exemplary embodiments only and not for the purpose of limiting the same, FIG. 1 schematically shows an exemplary imaging system 100 is shown and is generally identified by reference numeral 100. As can be seen, the imaging system 100 includes a programmed computing device 102 communicatively coupled to an ultrasound imaging system 104 and to a thermoacoustic imaging system 106. The ultrasound imaging system 104 and thermoacoustic imaging system 106 are configured to obtain ultrasound image data and thermoacoustic image data, respectively, of a region of interest 116. Components of the system 100 are shown in FIG. 1 as single elements. Such illustration is for ease of description, and it should be recognized that the system 100 may include multiple additional imaging devices or sub-devices.

The programmed computing device 102 may be a computer, server or other suitable processing device comprising, for example, a processing unit comprising one or more processors, computer-readable system memory (volatile and/or non-volatile memory), other non-removable or removable computer-readable memory (e.g., a hard disk drive, RAM, ROM, EEPROM, CD-ROM, DVD, flash memory, etc.) and a system bus coupling the various computer components to the processing unit. The computing device 102 may also comprise networking capabilities using Ethernet, Wi-Fi, and/or other suitable network format, to enable connection to shared or remote drives, one or more networked computers, or other networked devices. One or more input devices, such as a mouse and a keyboard (not shown) are coupled to the computing device 102 for receiving operator input. A display device (not shown), such as one or more computer screens or monitors, is coupled to the computing device 102 for displaying one or more generated images that are based on ultrasound image data received from the ultrasound imaging system 104 and/or the thermoacoustic image data received from thermoacoustic imaging system 106. The programmed computing device 102 executes program code stored on the computer-readable system memory and/or other non-removable or removable computer-readable memory and performs methods according to the program code as will be described further below.

The ultrasound imaging system 104 comprises an acoustic receiver in the form of an ultrasound transducer 108 that houses one or more ultrasound transducer arrays configured to emit sound waves into the region of interest 116. Sound waves directed into the region of interest 116 echo off materials within the region of interest 116, with different materials reflecting varying degrees of sound. Echoes that are received by the one or more ultrasound transducer arrays of the ultrasound transducer 108 may be processed by the ultrasound imaging system 104 before being communicated as ultrasound image data to the computing device 102 for further processing and for presentation on the display device as ultrasound images that can be interpreted by an operator. In one embodiment, the ultrasound imaging system 104 utilizes B-mode ultrasound imaging techniques assuming a nominal speed of sound of 1,540 m/s. As ultrasound imaging systems are known in the art, further specifics of the ultrasound imaging system 104 will not be described further herein.

The thermoacoustic imaging system 106 comprises an acoustic receiver in the form of a thermoacoustic transducer 110. The thermoacoustic transducer 110 houses one or more thermoacoustic transducer arrays. Radio-frequency (RF) applicator 112 may be housed together or separately from the thermoacoustic transducer 110. The RF applicator 112 is configured to emit short pulses of RF energy that are directed into the region of interest 116, which contains blood vessel 128. In one embodiment, the RF applicator 112 has a frequency between about 10 Mhz and 100 GHz and has a pulse duration between about 0.1 nanoseconds and 10 microseconds. RF energy pulses delivered to materials within the region of interest 116 induce acoustic pressure waves (thermoacoustic multi-polar signals) within the region of interest 116 that are detected by the thermoacoustic transducer 110. Acoustic pressure waves that are detected by the thermoacoustic transducer 110 are processed and communicated as thermoacoustic image data to the computing device 102 for further processing and for presentation on the display device as thermoacoustic images that can be interpreted by the operator.

In one embodiment, an optical transducer 113 is coupled to the RF applicator 112. In one embodiment, the optical transducer 113 is coupled to the RF emitter 1018 at an aperture 1006 of the waveguide 702.

In one embodiment, the optical transducer 113 is a device can include three ports: an optical input, an optical output, and an acoustics input port. The presence of an acoustic waveform at the acoustic input port affects the properties of the outgoing light with respect to the incoming light. For example, such properties can be intensity, polarization, phase, frequency, direction, or spatial distribution.

The coordinate system of the one or more ultrasound transducer arrays of the ultrasound transducer 108 and the coordinate system of the one or more thermoacoustic transducer arrays of the thermoacoustic transducer 110 are mapped by the computing device 102 so that acquired ultrasound and thermoacoustic images can be registered. Alternatively, the thermoacoustic imaging system 106 may make use of the one or more ultrasound transducer arrays of the ultrasound transducer 108 by disconnecting the one or more ultrasound transducer arrays from the ultrasound transducer 108 and connecting the one or more ultrasound transducer arrays to the thermoacoustic transducer 110. As will be appreciated, by doing this coordinate mapping between the one or more ultrasound transducer arrays and the one or more thermoacoustic transducer arrays is not required.

In one embodiment (shown in FIG. 1), an exemplary region of interest 116 contains a blood vessel 128 and is located within a liver 230 of a human or animal body (patient) 114. Patient 114 comprises a skin 202 and subcutaneous fat layer 218 and muscle layer 220 adjacent to liver 230.

Figure 2:
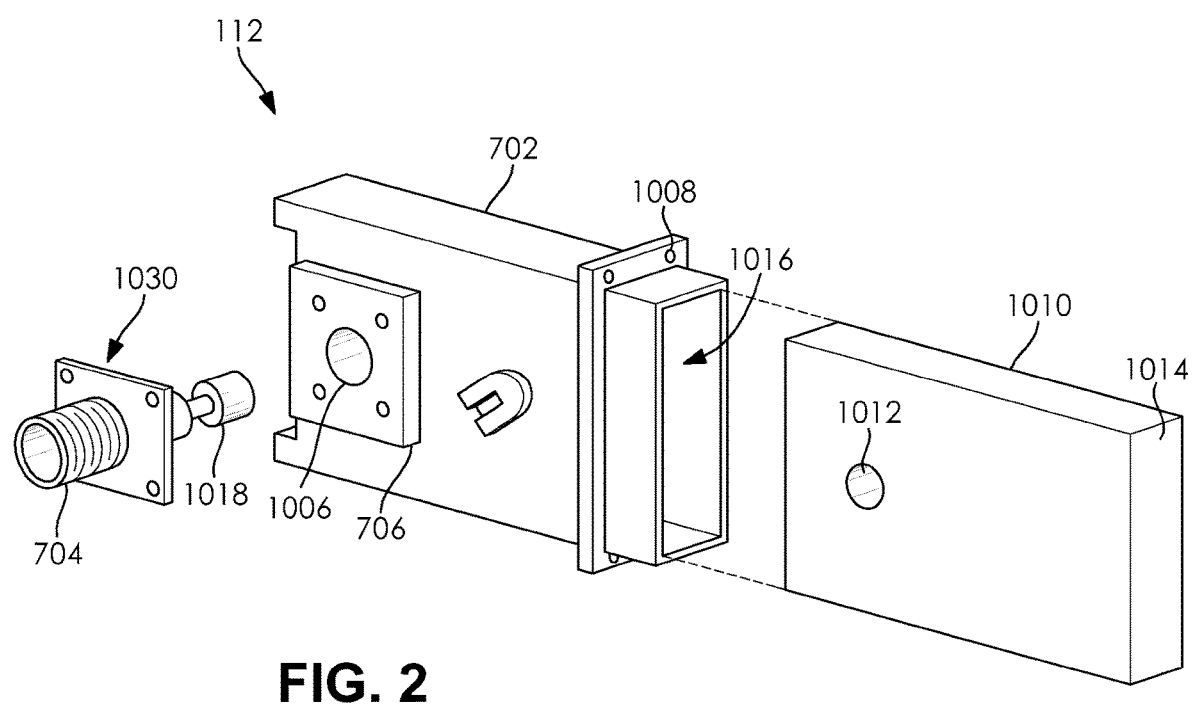
FIG. 2 shows an exemplary radio-frequency applicator 112.

FIG. 2 shows an exemplary radio-frequency applicator 112. As can be seen, the RF applicator 112 comprises a hollow, generally rectangular, open-ended waveguide 702, which can be formed of electrically conductive metal material. A plinth 706 is provided on a surface of the waveguide 702 adjacent one end thereof. A central aperture 1006 is provided in the plinth 706 and extends through the surface of the waveguide 702. A flange 1008 can extend about the waveguide 702 adjacent the other end thereof and can be utilized to mount the RF applicator 112 within a thermoacoustic probe which includes thermoacoustic transducer 110 and may include ultrasound transducer 108.

A solid, low loss, high dielectric constant insert 1010 formed of ceramic or other suitable material is positioned within the interior of the waveguide 702 and can fill the internal volume of the waveguide 702. A recess 1012 is provided in the high dielectric constant insert 1010 that is aligned with the aperture 1006. In one embodiment, high dielectric constant refers to a real relative permittivity greater than 10 and low loss refers to a loss tangent less than 0.01.

Insert 1010 has a surface facing 1014 which lies substantially flush with waveguide opening 1016. The opening 1016 is configured for electromagnetic energy communication therethrough. The opening 1016 is rectangular-shaped, but various sizes and shapes of the opening may be used in various embodiments, consistent with the opening being configured for electromagnetic energy communication therethrough.

An RF source 1030 having an RF emitter 1018 at one end that is configured to generate RF energy pulses, extends through the aperture 1006 and into waveguide 702 so that the RF emitter 1018 is suspended within waveguide 702. The RF source 1030 further includes a threaded connector 704 to which control electronics may be connected. In one embodiment, the RF source 1030 is configured to engage the plinth 706 and through which threaded fasteners pass. A mounting flange 1030 that overlies the plinth 706 to secure the RF emitter 1018 within the waveguide 702. The RF emitter 1018 functions as an internal radio frequency source for the waveguide 702.

In one embodiment, which may be desirable in medical applications that enable thermoacoustic measurements in tissue, the electromagnetic matching layer 710 has the following electromagnetic properties at a target frequency range between 15 MHz and 2.5 GHz: A) a real part of permittivity in a range from 5 to 65; and B) an imaginary part of the permittivity in a range 0 to 60.

For various applications, such as medical applications, the electromagnetic matching layer 710 may have the following acoustic properties at a target frequency range between 0.1 MHz and 20 GHz: A) a speed of sound greater than 2000 m/s; B) a density greater than 1500 kg/m^3; and C) an acoustic impedance greater than 3 MRayl (acoustic impedance is the speed of sound times the density).

For various applications, such as medical applications, the electromagnetic matching layer 710 can be formed of high permittivity elastomers (e.g., Avient's Preperm®), ceramics (e.g., National Magnetics' k-60®), and/or composite materials which contain high-permittivity particles embedded in a solid matrix (e.g., PPG's Des-K®).

In one embodiment, which may be desirable in ground-penetrating thermoacoustic measurements, the electromagnetic matching layer 710 can have the following electromagnetic properties at a target frequency range between 1 MHz and 1000 MHz: A) a real part of permittivity in a range from 2 to 80; and B) an imaginary part of the permittivity in a range 0 to 60.

For various applications, such as ground-penetrating thermoacoustic applications, the electromagnetic matching layer 710 can have the following acoustic properties at a target frequency range between 0.01 MHz and 100 GHz: A) a speed of sound greater than 500 m/s; B) a density greater than 2000 kg/m$\hat{\varphi}$3; and C) an acoustic impedance greater than 1 MRayl (acoustic impedance is the speed of sound times the density).

In one embodiment, which may be desirable for making underwater thermoacoustic measurements, the electromagnetic matching layer 710 has the following electromagnetic properties at a target frequency range between 3 kHz and 30 kHz: A) a real part of permittivity in a range from 2 to 100; and B) an imaginary part of the permittivity in a range 0 to 60.

For various applications, such as underwater thermoacoustic applications, the electromagnetic matching layer 710 has the following acoustic properties at a target frequency range between 50 kHz and 500 kHz: A) a speed of sound greater than 2000 m/s; B) a density greater than 2000 kg/m$\hat{\varphi}$3; and C) an acoustic impedance greater than 4 MRayl (acoustic impedance is the speed of sound times the density).

In one embodiment, the electromagnetic matching layer 710 is formed of the same material as the absorption layer 711.

Figure 3A:
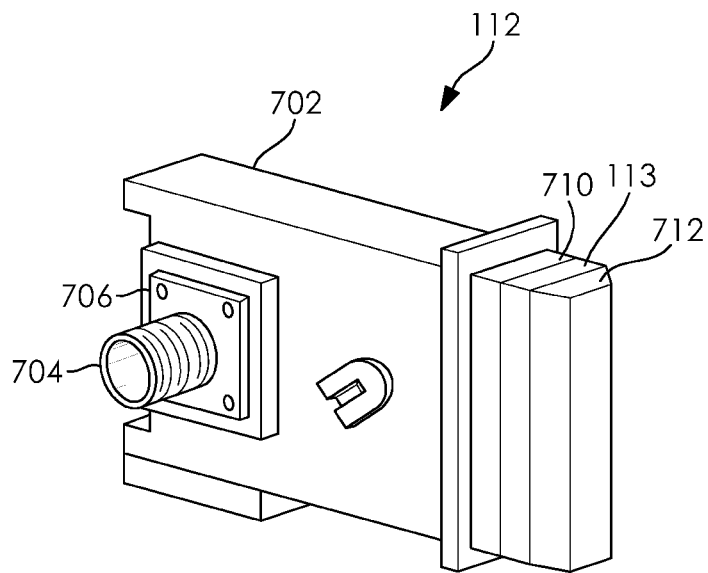
FIGS. 3A-3B show a perspective views of embodiments of a radio-frequency applicator.

FIG. 3A shows a perspective view of an exemplary radio-frequency applicator 112 embodiment. As FIG. 3A shows, the RF applicator 112 can include an RF waveguide 702, an electromagnetic matching layer 710, an optical transducer 113, and an acoustic matching layer 712. The exemplary acoustic matching layer 712 may include a cloth layer and foam layer. The exemplary acoustic matching layer 712 is shown with tapered edges, although many shapes and configurations are contemplated.

The exemplary acoustic matching layer 712 is configured to isolate signals from the radio-frequency applicator 112 from the thermoacoustic transducer 110 and the electronics (not shown) thereof. For example, the acoustic matching layer 712 may be configured to scatter or reflect the signal. The first acoustic absorbing material of the acoustic matching layer 712 can cause an acoustic impedance mis-match (e.g., a speed of sound mis-match, density mis-match, or both), elastic scattering (e.g., acoustic waves spread out), inelastic scattering (e.g., energy lost in the form of heat), or visco-elastic (e.g., vibration energy is converted to heat in the material deformation process). In some embodiments, it may be desirable for the first acoustic absorbing material to have a density of less than about 1 g/cm$^3$, less than about 0.5 g/cm$^3$, or less than about 0.25 g/cm$^3$. In some embodiments, it may be desirable for the first acoustic absorbing material to have a cell size of about 20 to 60 mm, about 30 to 55 mm, or about 35 to 50 mm. In the example described herein, the first acoustic absorbing material is cork, though it is intended that other acoustic absorbing materials consistent with this disclosure may be utilized. Other acoustic absorbing materials can include ester foams, ether foams, viscoelastic foams, high resiliency foams, and the like.

In some embodiments, it may be desirable for the acoustic absorbing material to have a cell size of about 150 to 400 mm, about 200 to 350 mm, or about 250 to 350 mm. For example, the acoustic absorbing material can be a polyurethane foam, though it is intended that other acoustic absorbing materials consistent with this disclosure may be utilized. Other acoustic absorbing materials can include styrene-acrylonitrile foam and the like.

In one embodiment, the acoustic matching layer 712 may be formed of open-cell foams, since foam has high acoustic attenuation. In a separate embodiment, an open-cell foam can be soaked with saline or other another liquid to modify its acoustic and electro-magnetic properties to match desirable ranges.

In one embodiment, the acoustic matching layer 712 is formed of impregnated cork, wherein particles used for impregnating it are chosen in such a manner they tune the cork to match the desired ranges. In one embodiment, the acoustic matching layer 712 is commercially available acoustic anechoic absorber (e.g., Precision acoustics' Aptflex®). The acoustic matching layer 712 can also be formed of Sorbothane® and/or other rubber-based vibration isolation materials such as Neoprene® and Nitrile®.

The acoustic matching layer 712 is configured to account for the difference between the acoustic impedance of the RF applicator 112 and the acoustic impedance of the tissue being examined. The acoustic matching layer 712 can be used to increase the power radiated from a transducing element with a higher impedance into a surrounding acoustic medium with a lower acoustic impedance.

For various applications, such as medical applications, the acoustic matching layer 712, can have the following electromagnetic properties at the target frequency range between 15 MHz and 2.5 GHz: A) a real part of permittivity in a range from 5 to 65; and B) an imaginary part of permittivity in a range from 0 to 60.

The acoustic matching layer 712, may have the following acoustic properties at a target frequency range between 0.01 Hz and 100 Hz: A) An acoustic attenuation of greater than 1 dB/(cm*kHz); B) a speed of sound between 70 and 700 m/s; C) a density between 500 and 1500 kg/m$\hat\varphi$3; and D) an acoustic impedance should from 35 kRayl to 1 MRayl, (acoustic impedance is the speed of sound times the density).

For various applications, such as underwater thermoacoustic applications, the acoustic matching layer 712, can have the following electromagnetic properties at the target frequency range between 3 kHz and 30 kHz: A) a real part of permittivity in a range from 2 to 100; and B) an imaginary part of permittivity in a range from 0 to 60.

The acoustic matching layer 712, can have the following acoustic properties at a target frequency range between 50 kHz and 500 kHz: A) An acoustic attenuation from 3 dB/(cm*MHz) to 50 dB/(cm*MHz); B) a speed of sound between 80 and 2000 m/s; C) a density between 500 and 1500 kg/m$\hat\varphi$3; and D) an acoustic impedance should from 0.4 MRayl to 3 MRayl, (acoustic impedance is the speed of sound times the density).

Figure 3B:
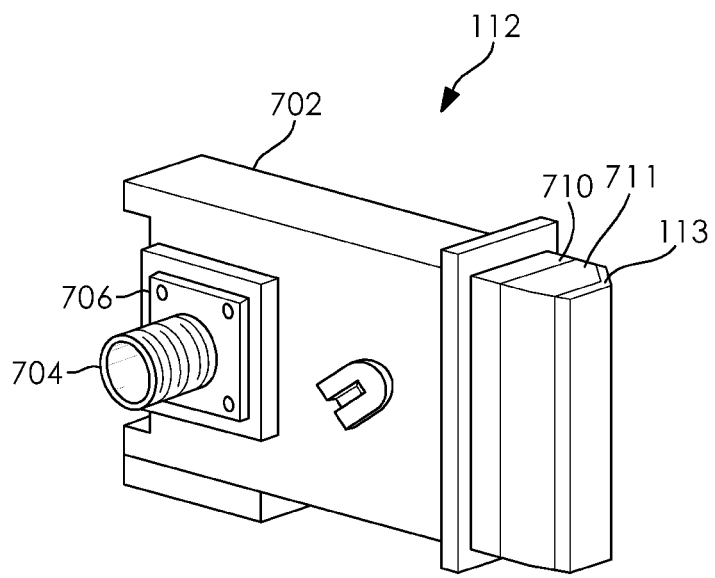

FIG. 3B shows a perspective view of an exemplary radio-frequency applicator 112 embodiment. As FIG. 3B shows, the RF applicator 112 can include an RF waveguide 702, an electromagnetic matching layer 710, an acoustic absorption layer 711, and an optical transducer 113. The exemplary acoustic absorption layer 711 may include a cloth layer and foam layer, and/or adhesive layer. The exemplary optical transducer 113 is shown with tapered edges, although many shapes and configurations are contemplated.

In one embodiment, the acoustic absorption layer 711 is formed of the same material as the electromagnetic matching layer 710 in order to have substantially the same acoustic properties.

In one embodiment, the acoustic absorption layer 711 is formed of can be formed of high permittivity elastomers (e.g., Avient's Preperm®), ceramics (e.g., National Magnetics' k-60®), and/or composite materials which contain high-permittivity particles embedded in a solid matrix (e.g., PPG's Des-K®).

For various applications, such as medical applications, the acoustic absorption layer 711, can have the following acoustic properties at a target frequency range between 0.1 MHz and 20 GHz: A) An acoustic attenuation from 0.3 dB/(cm*MHz) to 30 dB/(cm*MHz); B) a speed of sound between 1350 and 1650 m/s; C) a density between 900 and 1100 kg/m$\hat\varphi$3; and D) an acoustic impedance from 1.2 to 1.8 MRayl, which is close to tissue (1.5 MRayl) (acoustic impedance is the speed of sound times the density).

The acoustic absorption layer 711 can mitigate the generated spurious acoustic waves by: A) having strong acoustic scattering and/or absorption that mitigates the wave generated at the interface between the layer 711 and the applicator 112 from propagating further into the tissue; B) enforces a standoff between the tissue (e.g., skin 202 and/or fat 204) and the applicator 112. As the electromagnetic field peaks near the applicator 112 front face—this standoff reduces the electromagnetic field that reaches the highly conductive skin layer; C) Acts as an acoustic matched layer boundary around the applicator 112 and thus reduces strong acoustic reflections from this region; D) In one embodiment, the layer 711 is shaped to deflect signals away from the shortest perpendicular location from the RF emitter 1018.

In one embodiment, the absorption layer 711 has a cross-section of the shape is an arrow shape with an angle varying from 0-60 degrees and the vertex centered. In one embodiment, portions of the absorption layer 711 have a conical-shape or a partial conical-shape. In various embodiments, the absorption layer 711 includes portions having a frustal-conical shape, a pyramidal shape, frustum-pyramidal shape, or a parallelepiped shape. The optical transducer 113 may be coupled to the absorption layer 711 to continue the shape of the absorption layer forward.

Figure 4A:
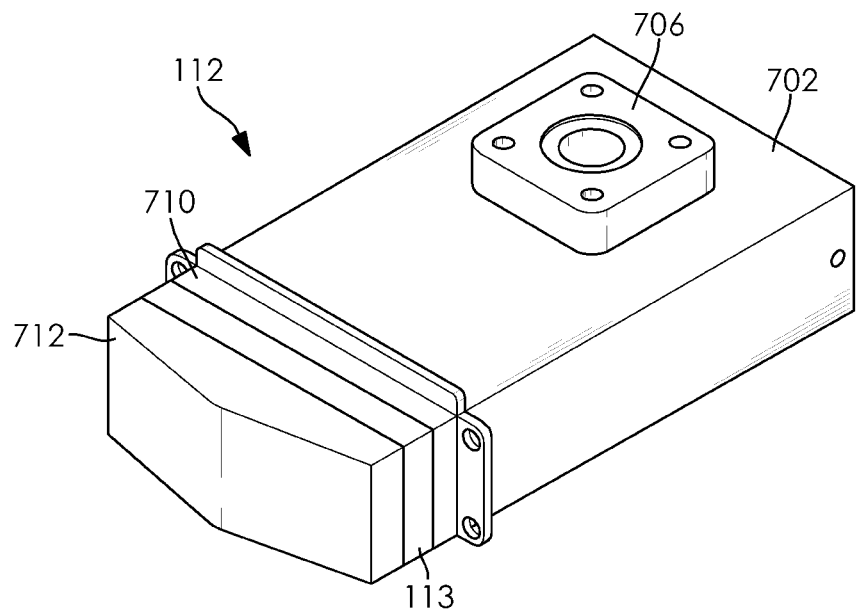
FIGS. 4A-4B show a perspective views of embodiments of a radio-frequency applicator.

FIG. 4A shows another embodiment of the radio-frequency applicator 112. As FIG. 4A shows, the acoustic matching layer 712 has a convex shape, i.e., tapered sides leading to a central edge, i.e., a lined vertex, on the leading surface. In this embodiment, the acoustic matching layer 712 has an arrow cross-sectional shape. While the optical transducer 113 is shown as flat or planar-shaped, it is contemplated herein that it may have be formed of many shapes including having tapered sides leading to a central edge.

In one embodiment, the acoustic matching layer 712 has a cross-section of the shape is an arrow shape with an angle varying from 0-60 degrees and the vertex centered. In one embodiment, portions of the acoustic matching layer 712 have a conical-shape or a partial conical-shape. In various embodiments, the acoustic matching layer 712 includes portions having a frustal-conical shape, a pyramidal shape, frustum-pyramidal shape, or a parallelepiped shape—all tapered or convex shaped in some manner to impinge a surface of a patient's skin, creating a concave surface to abut.

Figure 4B:
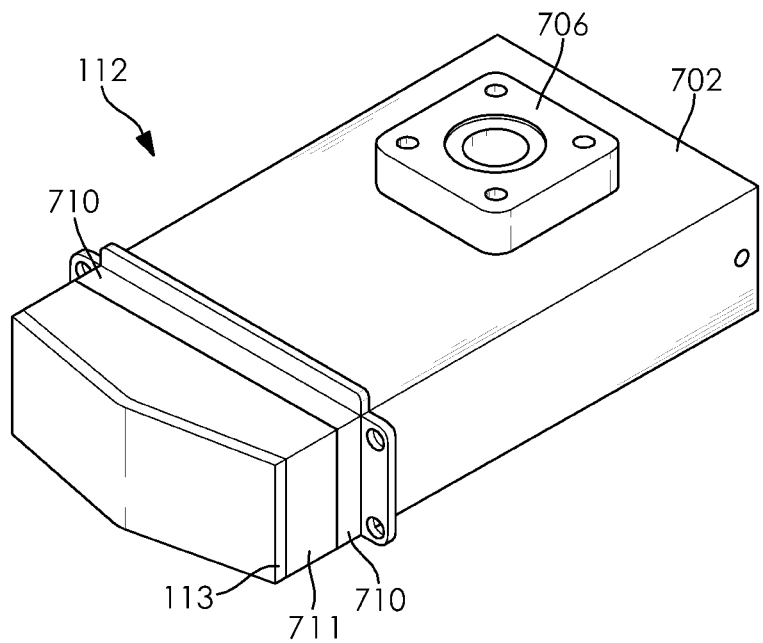

FIG. 4B shows another embodiment of the radio-frequency applicator 112 illustrating an exemplary shape of the optical transducer 113. As FIG. 4B shows, the optical transducer 113 has a convex shape, i.e., tapered sides leading to a central edge, i.e., a lined vertex, on the leading surface. In this embodiment, the optical transducer 113 has an arrow cross-sectional shape. In one embodiment, the optical transducer 113 forms a convex shape by continuing the shape of the absorption layer 711, which may be formed in many shapes including convex shaped which may be formed by having tapered sides leading to a central edge.

In one embodiment, the absorption layer 711 has a cross-section of the shape is an arrow shape with an angle varying from 0-60 degrees and the vertex centered. In one embodiment, portions of the absorption layer 711 have a conical-shape or a partial conical-shape. In various embodiments, the absorption layer 711 includes portions having a frustal-conical shape, a pyramidal shape, frustum-pyramidal shape, or a parallelepiped shape—all tapered or convex shaped in some manner to impinge a surface of a patient's skin, creating a concave surface to abut.

Figure 5A:
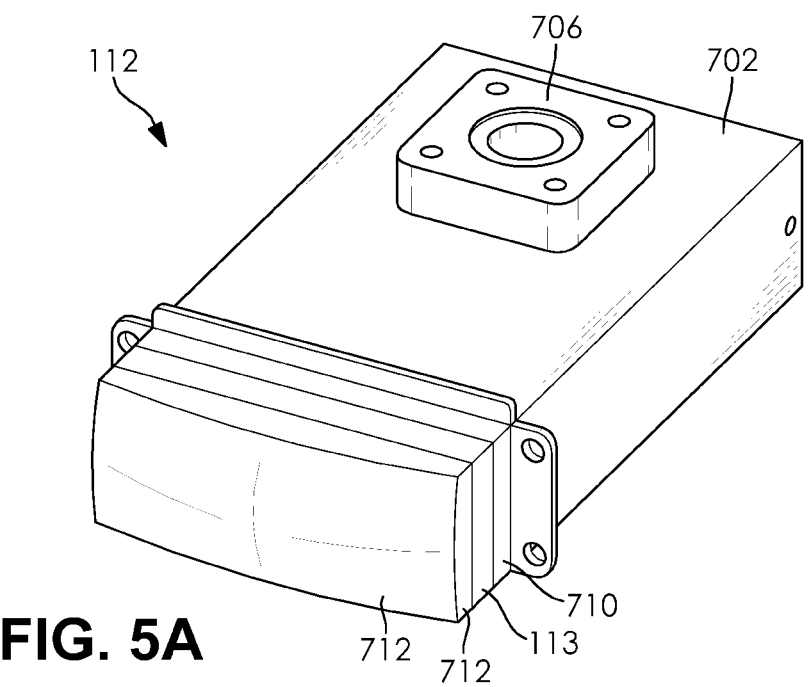
FIG. 5A shows another embodiment of the radio-frequency applicator illustrating an exemplary shape of an acoustic matching layer.

FIG. 5A shows another embodiment of the radio-frequency applicator 112 illustrating an exemplary shape of the acoustic matching layer 712. As FIG. 5A shows, the acoustic matching layer 712 has another type of convex shape, i.e., a rounded leading surface, i.e., a bulged central vertex. It is contemplated herein that other embodiments having a vertex in a central region of a leading surface of the acoustic matching layer 712 similar to the embodiment of FIG. 5A may be used. While the optical transducer 113 is shown as flat or planar-shaped, it is contemplated herein that it may be formed of many shapes including a rounded leading surface, i.e., a bulged central vertex to match the shape of the acoustic matching layer 712.

Figure 5B:
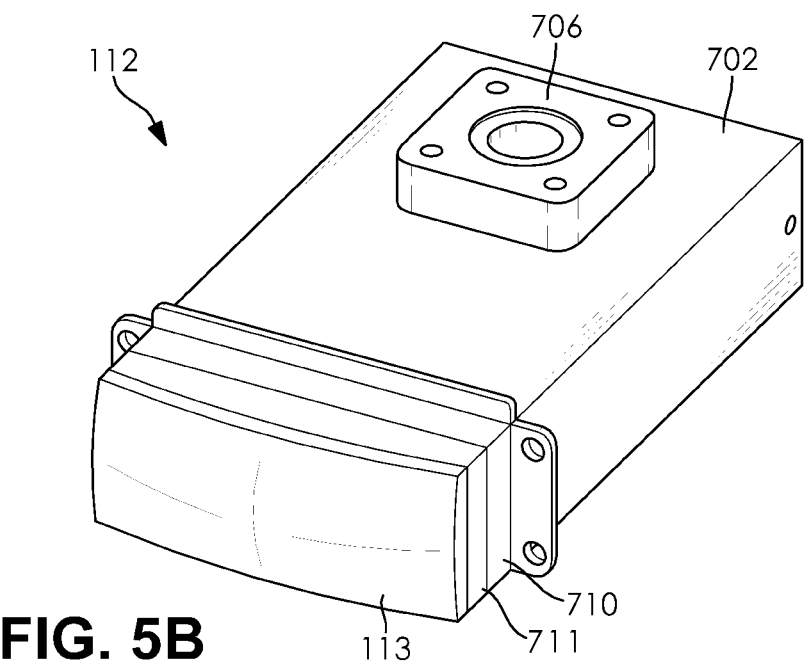
FIG. 5B shows another embodiment of the radio-frequency applicator illustrating an exemplary shape of the acoustic absorption layer.

FIG. 5B shows another embodiment of the radio-frequency applicator 112 illustrating an exemplary shape of the absorption layer 711. As FIG. 5A shows, absorption layer 711 has another type of convex shape, i.e., rounded leading surface, i.e., a bulged central vertex. It is contemplated herein that other embodiments having a vertex in a central region of a leading surface of the absorption layer 711 similar to the embodiment of FIG. 5B may be used. While the acoustic optical transducer 113 is shown as flat or planar-shaped, it is contemplated herein that it may be formed of many shapes including having a rounded leading surface, i.e., a bulged central vertex to match or continue the shape of the absorption layer 711 forward to an end of the applicator 112.

Figure 6:
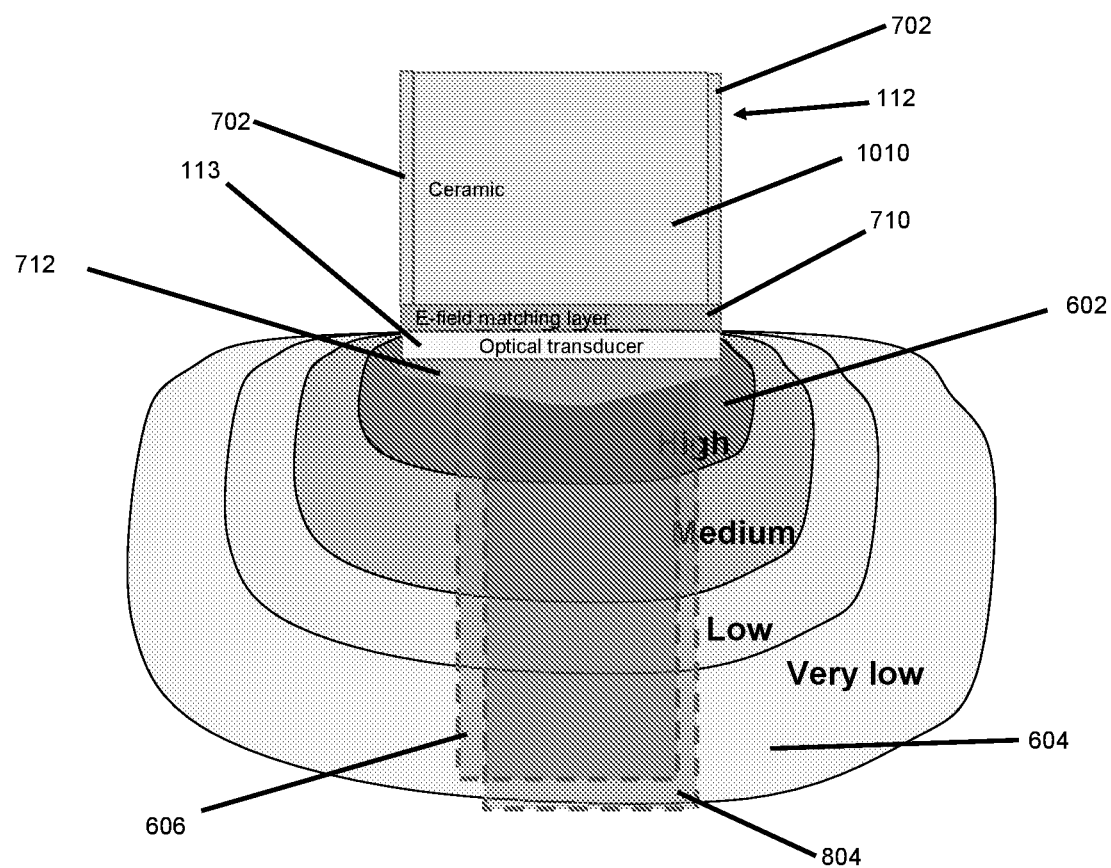
FIG. 6 schematically shows portions of an exemplary RF applicator to graphically illustrates an exemplary effect in an exemplary medium such as tissue with a convex shaped acoustic matching layer.

FIG. 6 schematically shows portions of the RF applicator 112 and graphically illustrates an exemplary effect in an exemplary medium such as tissue. As FIG. 6 shows, the applicator 112 includes an electromagnetic matching layer 710, an optical transducer 113, and an acoustic matching layer 712. In one embodiment, the acoustic matching layer 712 coupled to the optical transducer 113 and is configured to limit acoustic attenuation to 0.01 to 0.5 dB/(cm*MHz) with an acoustic frequency between 50 kHz and 25 MHz.

As FIG. 6 shows, the acoustic matching layer 712 may have a triangular-cross sectional shape, or, as described hereinabove, have a convex shape configured to impinge a concave shape upon a patient's skin when pressed with mild pressure.

FIG. 6 further shows comparable energy deposition rates for RF applicator 112. Tissue more proximate to the applicator 112, such as portion 602, is associated with higher energy deposition rate than tissue further away, e.g., portion 604. A volume of tissue, such as exemplary tissue 606, is the volume of tissue that is perpendicular to the location where RF energy exits the RF applicator 112 and is associated with a maximized energy deposition rate.

Because the optical transducer 113 is attached to the RF emitting opening of the RF applicator 112 it results in a match between the maximized energy deposition rate 302 and a peak optical transducer sensitivity 804.

In one embodiment, the shape of the acoustic matching layer 712 causes an indentation in a patient's skin when pressed thereto. During operation, plane waves can travel perpendicular to the direction of the skin indentation and subcutaneous fat interface. Hence, the plane wave effect on thermoacoustic signals from the fat and muscle interface and the region of interest 116 is minimized, since it no longer travels directly toward the region of interest 116.

Figure 7:
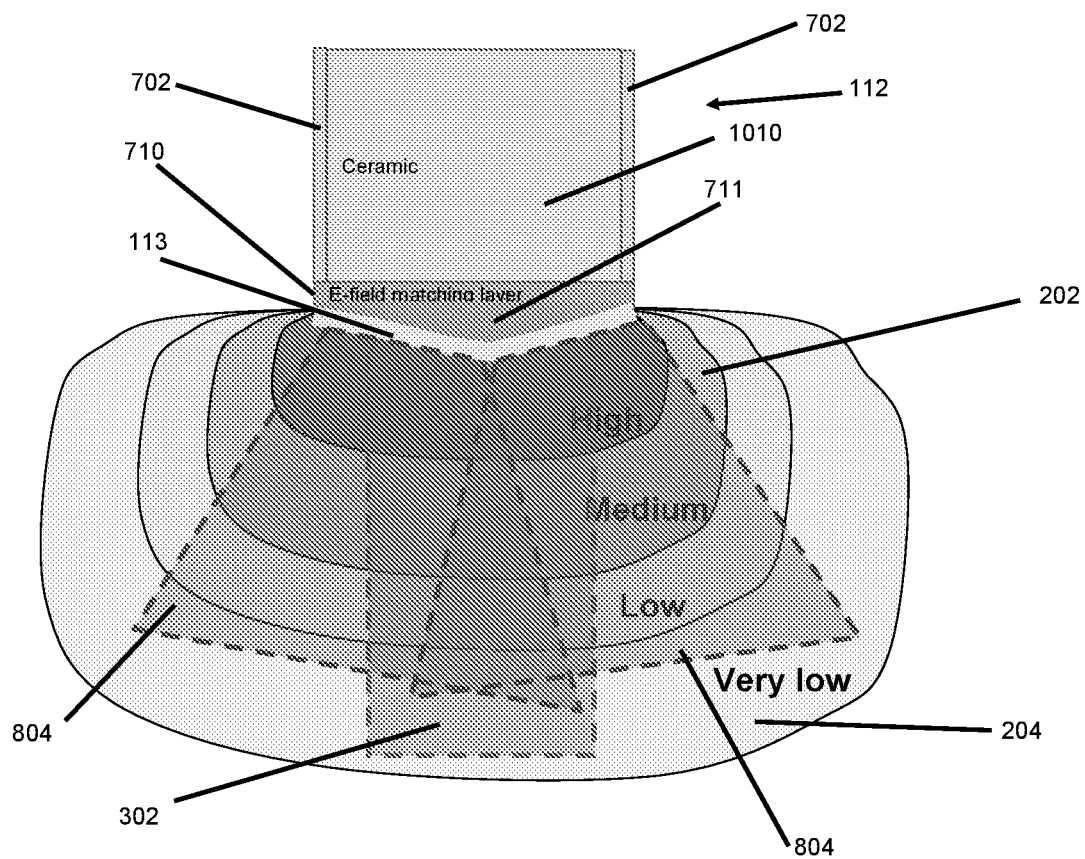
FIG. 7 schematically shows portions of an exemplary RF applicator to graphically illustrates an exemplary effect in an exemplary medium such as tissue with a convex shaped end associated with an optical transducer.

FIG. 7 shows portions of an exemplary RF applicator 112 having at least one radio frequency source. The applicator 112 includes an electromagnetic matching layer 710 coupled to a shaped acoustic absorption layer 711, and an optical transducer 113. In one embodiment, the acoustic absorption layer 711 is configured to limit acoustic attenuation to 0.01 to 0.5 dB/(cm*MHz) with an acoustic frequency between 50 kHz and 25 MHz (in one embodiment, wedge 1002). In one embodiment, the optical transducer 113 is coupled to the RF emitter 1018.

As FIG. 7 shows, the acoustic absorption layer 711 may have a triangular-cross sectional shape, or, as described hereinabove, have a convex shape. The optical transducer 113 can be shaped to bring forward the shape of the acoustic absorption layer 711 so that when the optical transducer 113 is pressed into a patient's skin it impinges a concave shape thereto.

In a separate embodiment, the RF applicator 112 structure further includes an electromagnetic matching layer that is placed between the optical transducer 113 and an acoustically matching layer, is coupled to both the optical transducer 113 and the acoustically matching layer, and prevents contact between the optical transducer 113 and the acoustically matching layer.

In a separate embodiment, RF applicator 112 structure includes an electromagnetic matching layer that is placed between radio-frequency (RF) emitter which includes at least one radio frequency source and the optical transducer 113.

In a separate embodiment, electromagnetic matching layer 710 is integral to the acoustically matching layer 712.

While the foregoing disclosure discusses illustrative embodiments, it should be noted that various changes and modifications could be made herein without departing from the scope of the described embodiments as defined by the appended claims. Accordingly, the described embodiments are intended to embrace all such alterations, modifications and variations that fall within scope of the appended claims. Furthermore, although elements of the described embodiments may be described or claimed in the singular, the plural is contemplated unless limitation to the singular is explicitly stated. Additionally, all or a portion of any embodiment may be utilized with all or a portion of any other embodiments, unless stated otherwise.

We claim:

1. A thermoacoustic probe for a thermoacoustic imaging system, the probe comprising:
   a radio-frequency (RF) applicator having an insert, wherein the applicator is configured to transmit at least one radio frequency source;
   an electromagnetic matching layer coupled to the insert of the RF applicator;
   an optical transducer that is coupled to the electromagnetic matching layer; and
   an acoustic matching layer that is coupled to the optical transducer.

2. The thermoacoustic probe of claim 1, wherein the acoustic matching layer is configured to limit acoustic attenuation to 0.01 to 0.5 dB/(cm*MHz) with an acoustic frequency between 50 kHz and 25 MHz.

3. The thermoacoustic probe of claim 1, wherein the optical transducer is coupled to an RF emitter at an aperture of the RF applicator.

4. The thermoacoustic probe of claim 1, wherein a cross-sectional shape of the acoustically matching layer comprises a triangular shape with a center vertex between 90 degrees and 180 degrees.

5. The thermoacoustic probe of claim 1, wherein portions of the acoustically matching layer are formed in convex shape.

6. The thermoacoustic probe of claim 1, wherein the acoustically matching layer has at least one tapered edge.

7. The thermoacoustic probe of claim 1, wherein the acoustic matching layer, at a frequency range between 15 MHz and 2.5 GHz, has a real part of permittivity from 5 to 65 and an imaginary part of permittivity from 0.01 to 60.

8. The thermoacoustic probe of claim 1, wherein the acoustic matching layer, at a frequency range between 50 kHz and 25 MHz, has an acoustic impedance between 1.2 MRayl and 1.8 MRayl.

9. The thermoacoustic probe of claim 1, wherein the acoustic matching layer is formed of an open-cell foam.

10. The thermoacoustic probe of claim 1, wherein the acoustic matching layer is formed of an acoustic anechoic absorber.

11. The thermoacoustic probe of claim 1, wherein the acoustic matching layer is formed of a rubber-based vibration isolation material.

12. The thermoacoustic probe of claim 1, wherein the electromagnetic matching layer, at a frequency range between 15 MHz and 2.5 GHz, has a real part of permittivity from 5 to 65 and an imaginary part of permittivity from 0.01 to 60.

13. The thermoacoustic probe of claim 1, wherein the electromagnetic matching layer is formed of an elastomer material with a permittivity from 23 to 60.

14. The thermoacoustic probe of claim 1, wherein the electromagnetic matching layer is formed of a ceramic material.

15. The thermoacoustic probe of claim 1, wherein the electromagnetic matching layer is formed of a composite material which contains particles with a permittivity from 23 to 60 embedded in a solid matrix.

16. The thermoacoustic probe of claim 1, wherein the optical transducer is configured to receive light-based information corresponding to at least one of light intensity, polarization, phase, frequency, direction, and spatial distribution.

17. A thermoacoustic probe for a thermoacoustic imaging system, the probe comprising:
   a radio-frequency (RF) applicator having an insert, wherein the applicator is configured to transmit at least one radio frequency source;
   an electromagnetic matching layer having first and second opposing sides, wherein the first opposing side of the electromagnetic matching layer is coupled to the insert of the RF applicator;
   an optical transducer having first and second opposing sides, wherein a first opposing side of the optical transducer is coupled to the second opposing side of the electromagnetic matching layer; and
   an acoustic matching layer that is coupled to the second opposing side of the optical transducer.

18. The thermoacoustic probe of claim 17, wherein the optical transducer is configured to receive light-based information corresponding to at least one of light intensity, polarization, phase, frequency, direction, and spatial distribution.

19. The thermoacoustic probe of claim 17, wherein the first opposing side of the electromagnetic matching layer is coupled to the insert of the RF applicator using an adhesive, the first opposing side of the optical transducer is coupled to the second opposing side of the electromagnetic matching layer using an adhesive, and the acoustic matching layer is coupled to the second opposing side of the optical transducer using an adhesive.

20. The thermoacoustic probe of claim 17, wherein the acoustic matching layer is configured to limit acoustic attenuation to 0.01 to 0.5 dB/(cm*MHz) with an acoustic frequency between 50 kHz and 25 MHz.

21. The thermoacoustic probe of claim 17, wherein the optical transducer is coupled to an RF emitter at an aperture of the RF applicator.

22. The thermoacoustic probe of claim 17, wherein at least a portion of a cross-sectional shape of the acoustically matching layer comprises a triangular shape with a center vertex between 90 degrees and 180 degrees.

23. The thermoacoustic probe of claim 17, wherein portions of the acoustically matching layer are formed in convex shape.

24. The thermoacoustic probe of claim 17, wherein the acoustically matching layer has at least one tapered edge.

25. The thermoacoustic probe of claim 17, wherein the acoustic matching layer, at a frequency range between 15 MHz and 2.5 GHz, has a real part of permittivity from 5 to 65 and an imaginary part of permittivity from 0.01 to 60.

26. The thermoacoustic probe of claim 17, wherein the acoustic matching layer, at a frequency range between 50 kHz and 25 MHz, has an acoustic impedance between 1.2 MRayl and 1.8 MRayl.

27. The thermoacoustic probe of claim 17, wherein the acoustic matching layer is formed of an open-cell foam.

28. The thermoacoustic probe of claim 17, wherein the acoustic matching layer is formed of an acoustic anechoic absorber.

29. The thermoacoustic probe of claim 17, wherein the acoustic matching layer is formed of a rubber-based vibration isolation material.

* * * * *